United States Patent [19]

Tanner

[11] 4,361,141
[45] Nov. 30, 1982

[54] SCOLIOSIS TRANSVERSE TRACTION ASSEMBLY

[75] Inventor: Gary D. Tanner, Warsaw, Ind.

[73] Assignee: Zimmer USA, Inc., Warsaw, Ind.

[21] Appl. No.: 61,344

[22] Filed: Jul. 27, 1979

[51] Int. Cl.³ .................................................. A61F 5/04
[52] U.S. Cl. ..................................... 128/69; 128/92 R
[58] Field of Search ............... 128/69, 83, 92 A, 92 B, 128/92 R, 84 R, 84 B

[56] References Cited

U.S. PATENT DOCUMENTS

| | | | |
|---|---|---|---|
| 1,411,013 | 3/1922 | Gilmore | 269/240 |
| 2,497,626 | 2/1950 | Persall | 128/92 A |
| 3,693,616 | 9/1972 | Roaf et al. | 128/69 |
| 3,862,631 | 1/1975 | Austin | 128/92 B |
| 4,041,939 | 8/1977 | Hall | 128/92 B |
| 4,078,559 | 3/1978 | Nissinen | 128/69 |
| 4,187,841 | 2/1980 | Knutson | 128/92 A |
| 4,257,409 | 3/1981 | Bacal et al. | 128/69 |

FOREIGN PATENT DOCUMENTS

| | | | |
|---|---|---|---|
| 2244446 | 4/1975 | France. | |
| 485739 | 9/1975 | U.S.S.R. | 128/69 |

Primary Examiner—Robert W. Michell
Assistant Examiner—T. J. Wallen
Attorney, Agent, or Firm—Margaret L. Geringer; Richard H. Brink

[57] ABSTRACT

An apparatus for the correction of scoliotic curvature of the spinal column. A Harrington distraction rod engages a concave side of the curvature of the spinal column and a Harrington compression rod engages a convex side of the curvature of the spinal column. A tensioning device engages the Harrington distraction rod and the Harrington compression rod so that the rods may be drawn toward each other or otherwise held in position with respect to each other. The tensioning device is comprised of a transverse threaded rod having a basket hook at an end thereof. The threaded rod engages the basket hook via a swivel connection which allows the transverse rod to rotate about its longitudinal axis within the basket hook. The other end of the threaded rod has a knurled end to facilitate handling. The basket hook is preferably used to engage the Harrington compression rod and has thread engagers which positively lock the basket hook onto the Harrington compression rod and prevent movement of the basket hook along the Harrington compression rod. A transverse hook for engaging the Harrington distraction rod threadably engages the transverse rod of the tensioning device. A nut is located on the transverse rod of the tensioning device to lock the position of the transverse hook. To engage the tensioning device, a bone clamp or similar instrument is first used to draw the Harrington distraction and compression rods toward each other, maintaining the desired amount of transverse tension. The basket hook is placed on the Harrington compression rod and the knurled end of the transverse threaded tensioning rod is rotated, causing the transverse hook to move along the transverse threaded rod until the transverse hook snugly engages the Harrington distraction rod. At this point, the bone clamp is removed, and the nut is tightened down as a safety lock.

11 Claims, 8 Drawing Figures

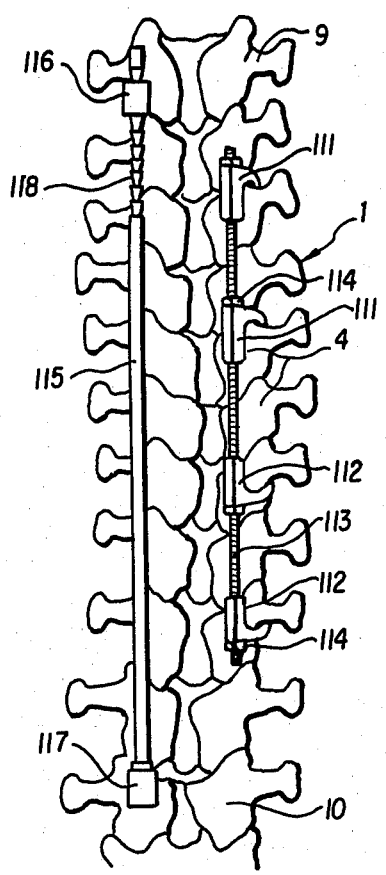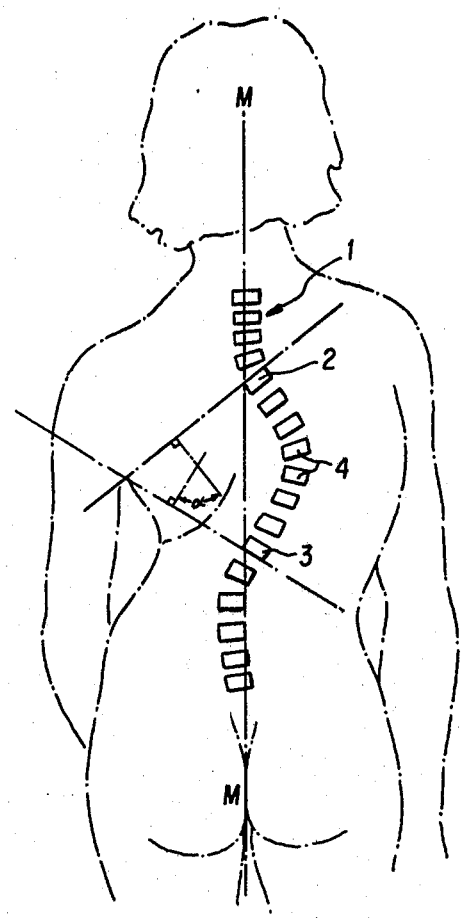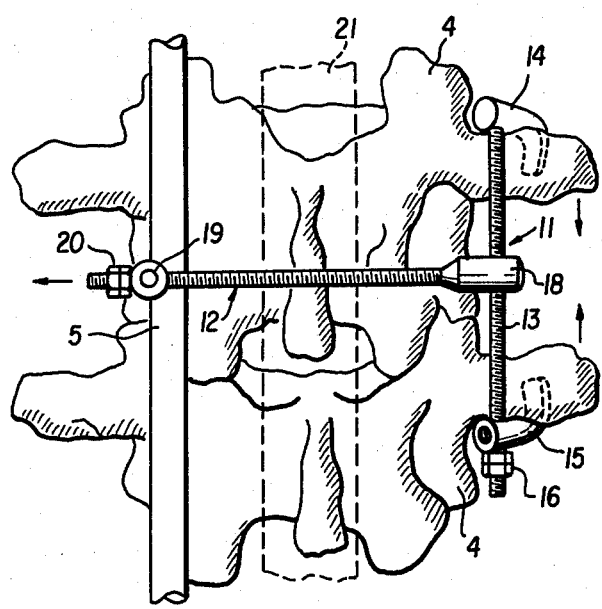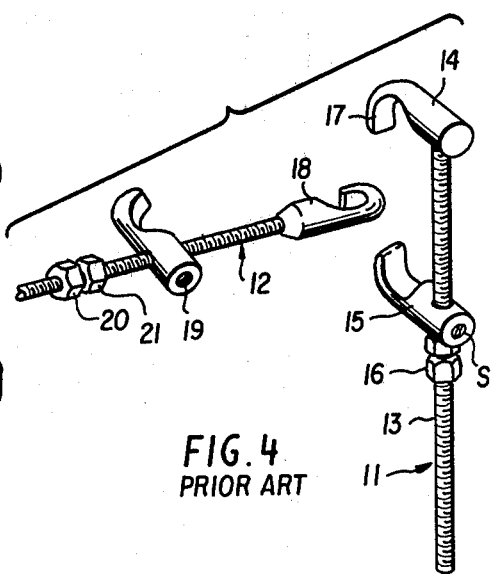
FIG. 1
FIG. 2
FIG. 3 PRIOR ART
FIG. 4 PRIOR ART

SCOLIOSIS TRANSVERSE TRACTION ASSEMBLY

BACKGROUND OF THE INVENTION

1. Field of the Invention

The invention generally relates to a device for straightening the spine in use in a surgical treatment for deviations of the spinal column, especially scoliosis. In particular, the present invention relates to a transverse traction device for inter-engaging a Harrington compression rod and a Harrington distraction rod which are affixed to the spine.

2. Description of the Prior Art

Scoliosis is the lateral deviation of the spinal column. The spinal curvature which results from scoliosis is generally defined on the basis of specific reference points. In particular, the extreme upper and lower vertebrae and the most displaced vertebrae are of particular interest. The extreme upper and lower vertebrae are those which are the most inclined relative to the median longitudinal axis of the torso. The two planes within which the extreme upper and lower vertebrae can be found define the scoliotic angle. The most displaced vertebra is defined as the vertebra which is the farthest from the median axis of the torso.

When the scoliotic angle of curvature exceeds a given limit of approximately 35°–50°, it becomes necessary to consider surgical treatment of the scoliosis. The surgical treatment is known as arthrodesis and consists of fusing together the vertebrae of the scoliotic curvature, after correcting the scoliotic curvature to the maximum possible extent by straightening and opening. Such correction can be accomplished prior to the operation by continuous traction of the spine or by corrective plaster casts.

However, it is during surgery that the correction is completed and finalized. For this purpose, a solid rod with hooks is placed in the concavity of the curvature and a threaded rod with hooks is placed on the convexity of the curvature. These rods straighten the spine and maintain the correction until arthrodesis is attained by means of autogenous bone graft. The implants used most often to correct curvature during surgery are known as the Harrington distraction system and the Harrington compression system, illustrated in FIG. 1.

The distraction system consists of two metallic anchoring devices 116 and 117 of the hook type, which are attached to the vertebrae 4 which comprise the spinal column, generally referred to by reference character 1. A notched metal rod 115 serves as a stay and permits the spacing between the hooks 116 and 117. One of the ends 118 of rod 115 is usually notched in such a manner as to permit the distance between anchoring devices 116 and 117 to be adjusted by means of a spreading instrument. Generally, the upper anchoring element 116 is intended for fastening toward the upper end of the spine and is hooked onto a dorsal vertebra 9. Usually, the hook of element 116 is directed upward and shaped in such a manner as to permit its insertion between the spinal apophysis and a transverse apophysis of that vertebra, between the upper and lower articular facets. The hook of element penetrates into the interarticular space and is supported on the vertebra.

Similarly, a lower anchoring element 117 is intended to be fastened at the lower end of the spine and is often supported on a lumbar vertebra 10. It is contemplated that the hook associated with element 117 is directed downwardly and supported on the blade of the lumbar vertebra between the spinal apophysis and the articular mass. In the illustrated example, vertebrae 9 and 10 are considered to be the extreme vertebrae.

The compression system consists of two or more metallic anchoring devices 111 and 112 of the hook type which are attached to selected transverse processes of vertebrae 4 which are situated on the convex side of the scoliotic curvature. Threaded metal rod 113 serves as a stay and permits spacing between the hooks 111 and 112. Hooks 111 and 112 usually face each other and slide freely along threaded rod 113. These hooks are adjusted by means of nuts 114 so as to effect compression of the convexity of the scoliotic curvature. It is understood that more than two hooks and nuts can be used to achieve the desired amount of compression.

Thus, by the application of Harrington distraction and compression systems, the straightening of the scoliotic curvature can be effected and maintained. Vertebral arthrodesis is then achieved by exposing the posterior arches of the vertebrae and attaching autogenous spony bone with the Harrington devices left in place.

FIG. 2 is an illustration of a patient suffering from scoliosis schematically represented from the rear. The spinal column 1 is visible and indicated schematically by rectangles or trapezoids. The patient illustrated in FIG. 2 exhibits a scoliosis involving a deviation of the vertebrae to the right. The scoliotic curvature can be defined on the basis of the top vertebra 2 and the bottom vertebra 3 of the deviation, and the vertebrae 4 which are located at the peak of the curvature. It is noted that the vertebrae 2 and 3 are those which are most strongly inclined relative to the median longitudinal axis M—M of the body, while vertebrae 4 are those which are farthest from that axis. Angle $\alpha$ is thus a characteristic of the scoliotic curvature. When the angle $\alpha$ exceeds a limit of approximately 35°–50°, it is often necessary to resort to arthrodesis and to install Harrington distraction and compression systems rod, as illustrated in FIG. 1.

However, in an effort to further support the peak vertebrae 4 which are further away from the axis M—M than the other vertebrae and to further improve straightening of the scoliotic curvature, transverse tensioning devices as illustrated in FIGS. 3 and 4 have been suggested by French Pat. No. 2,244,446. Such a transverse tensioning device makes use of (1) a compression rod 11, similar to the Harrington compression rod, and (2) a tensioning element 12. Obviously, the intent of the Harrington distraction rod 5 is to separate the vertebrae apart from each other. The basis of the transverse tensioning device is a tensioning element 12 which connects the compression rod 11 on the side of the vertebrae most displaced by the curvature to the Harrington distraction rod 5. Preferably, the tensioning means is adjustable so that the peak of the scoliotic curvature can be pulled toward the distraction rod 5, resulting in a better correction of the curvature and a better preservation of the correction obtained. It is contemplated that a transverse tensioning device results in reduction of the lateral displacement of the most displaced vertebrae, completion of the correction obtained by the longitudinal Harrington distraction rod, and relief of the load on the supporting vertebrae.

Generally, the transverse tensioning devices of the prior art have been comprised of compression rod 11 and tensioning element 12, the first of which is intended to be supported on two vertebrae 4 which are closest to the peak of the scoliotic curvature, and the second of which permits the first to be brought nearer to the metallic distraction rod 5.

Compression rod 11 is generally comprised of a threaded rod 13, at one end of which is permanently fastened a hook 14. This rod 13 passes freely through another hook 15 which is held in place by nuts 16. Hook 15 slides along rod 13 and faces hook 14. Hook 14 has a rounded and beveled end 17 which allows it to be supported from top to bottom, by the transverse processes of the upper vertebra 4 of the peak, after cutting of the costo-transverse ligament. Hook 15 passes from the bottom to top beneath the transverse process of the lower vertebra 4 of the peak. Nut and locking nut 16 permit hooks 14 and 15 to be brought closer to each other and to be tightened in such a way as to effect a firm transverse grip. Hook 15 is finally locked into position by means of a set screw, which jams the threads of rod 11. Hooks 14 and 15 are attached to the transverse processes of vertebrae 4 which are situated on the convex side of the scoliotic curvature.

Tensioning element 12 comprises a threaded rod having one end which is permanently fastened to hook 18. The rod passes freely through another hook 19 which is held in place on the rod by nuts 20 and 21. Hook 19 is able to slide along the rod 12 and faces Hook 18. Hook 18 engages rod 13 and Hook 19 engages Harrington rod 5. By screwing nut 21 and locking nut 20 along the rod, hooks 18 and 19 approach each other and the peak vertebrae 4 are made to approach median axis M—M. This allows better correction of the scoliotic curvature. Hook 19 is finally locked into position by means of a set screw which jams the threads of element 12. It is noted that elements 11 and 12 are located at the posterior side of the spine, element 12 being in contact with the spongy graft 21 necessary for the arthrodesis so as to reinforce the solidity of the arthrodesis.

The surgical techniques used in employing the transverse traction device illustrated in FIGS. 3 and 4 are outlined in more detail by Dr. Cotrel in his article entitled "New Techniques for the Treatment of Idiopathic Scoliosis," *International Orthopedics,* Spring, 1978, pp. 247-265.

The basic problems with the above described transverse traction system are as follows:
1. It is difficult to apply.
2. It requires the use of additional instruments other than those commonly available to spinal surgeons famililar with the Harrington procedure.
3. It provides for the use of tiny set screws to positively locate hooks 15 and 19 on elements 11 and 12. Such set screws must be cut off flush with the hooks, thereby risking the loss of a portion of a set screw in the human body.
4. Hook 18 of element 12 does not positively locate on element 11 and is subject to slippage.

SUMMARY OF THE INVENTION

It is an object of this invention to describe a transverse traction apparatus for engaging a Harrington distraction rod and a Harrington compression rod.

It is a further object of this invention to describe a transverse traction apparatus having a basket hook at an end thereof which is connected by a swivel to a transverse rod, the basket hook for engaging a Harrington compression rod used for correcting scoliotic curvature of the spinal column.

It is yet another object of this invention to describe a transverse traction apparatus which includes a transverse hook for engaging a Harrington distraction rod used to correct scoliotic curvature of the spinal column.

It is a further object of this invention to describe an apparatus for transversely tensioning a Harrington distraction rod and a Harrington compression rod employed for correcting scoliotic curvature of the spinal column, the apparatus including a transverse rod having a knurled end which promotes ease of assembly and use.

It is a further object of this invention to describe a transverse traction apparatus for use in correcting scoliotic curvature of the spinal column which can be quickly and efficiently used to engage a Harrington distraction rod and a Harrington compression rod attached to the spinal column.

It is another object of this invention to describe a transverse traction apparatus for correcting scoliotic curvature of the spine which does not require the use of tools or instruments other than those commonly available to spinal surgeons.

The basis of the invention is a transverse traction device for engaging a Harrington distraction rod and a Harrington compression rod. Generally, in the treatment of scoliotic curvature of the spinal column, a Harrington distraction rod is placed on the concave side of the spine and a Harrington compression rod is placed on the convex side of the spine. A tensioning means is generally used to hold the distraction and compression rods in relative position and/or to draw the rods together. The transverse traction apparatus according to the invention includes a transverse rod which is threaded and terminates in a swivel joint for engaging a basket hook. The swivel joint allows the transverse rod to rotate about its longitudinal axis within the basket hook. The basket hook is generally used to engage the Harrington compression rod and has thread engagers which particularly engage the threads of the Harrington compression rod and prevent movement between the basket hook and the compression rod. A transverse hook is threaded onto the transverse rod for engaging the Harrington distraction rod. The end of the transverse rod which is opposite the basket hook has a knurled configuration so that the transverses rod may be rotated about its longitudinal axis. Rotation of the transverse rod causes the transverse rod to swivel within the basket hook which further causes the transverse hook to move along the transverse rod due to the threaded engagement between the transverse hook and the transverse rod. This allows the basket hook to engage the Harrington compression rod and the transverse hook to engage the Harrington distraction rod while the transverse rod is rotated by its knurled end. This enables a tensioning interconnection to be established between the two Harrington rods. When the transverse traction apparatus is in proper position, a locking nut which threadably engages the transverse rod is turned to meet the transverse hook and engage the transverse hook so that it is held in a locking position.

BRIEF DESCRIPTION OF THE DRAWINGS

These features and objects of the invention, as well as others, will become apparent to those skilled in the art by referring to the accompanying drawings in which:

FIG. 1 is an illustration of a Harrington distraction rod and Harrington compression rod engaging the spinal column;

FIG. 2 is a schematic illustration, from the rear, of an individual suffering from scoliotic curvature of the spinal column;

FIG. 3 shows a Harrington distraction rod engaging the spinal column along with a compression rod and transverse traction device as disclosed in French Pat. No. 2,244,446;

FIG. 4 is a perspective view of the compression rod and the transverse traction device of French Pat. No. 2,244,446;

DETAILED DESCRIPTION OF THE INVENTION

Figure 5:
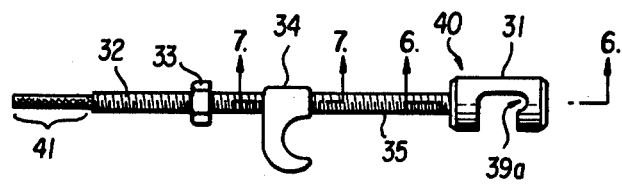
FIG. 5 is a perspective view of the transverse traction apparatus according to the invention.
Figure 6:
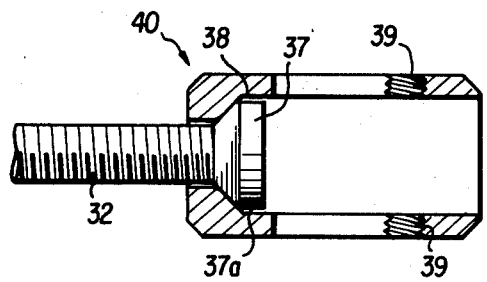
FIG. 6 is a sectional view of a portion of the transverse traction device taken along line 6—6 of FIG. 5 and showing the swivel connection between the transverse rod and the basket hook.

The basis of the invention is a transverse traction assembly which is convenient to use and provides significant advantages over the prior art transverse devices. In particular, the traction assembly, as illustrated in FIG. 5, includes a basket hook 31 which is generally employed to engage a Harrington compression rod 113, as shown in FIG. 1. The basket hook 31 is connected to a transverse rod 32 which is threaded and terminates in a swivel means generally referred to by reference character 40 for engaging the basket hook 31. The swivel means 40 allows the transverse rod to rotate about its longitudinal axis within the basket hook. As can be appreciated more fully by referring to the sectional illustration of FIG. 6, the swivel means 40 is comprised of a knob 37 which is an integral part of the transverse rod 32. Although the knob 37 illustrated in FIG. 6 is shown as having a cylindrical portion 37a which is integrally connected to a tapering portion which is integrally connected to the transverse rod 32, it is contemplated that any convenient knob system may be employed to form the swivel means. For example, a ball or frusto-conical structure may be employed. The basket hook 31 forms a seat 38 which has a shape complementary to the knob 37 and engages the knob 37. Preferably, the seat 38 and knob 37 are smooth so that the transverse rod 32 may freely rotate about its longitudinal axis with respect to the basket hook 31. However, it is alternatively contemplated that the knob 37 may have projections which engage concavities located within the seat 38 to restrict rotation between the basket hook 31 and transverse rod 32 when the entire system is in an engaged position.

The other end of the transverse rod 32 forms a knurled end 41 which is used to rotate the transverse rod 32 by a simple twirling action between the thumb and index finger. However, it is contemplated that the knurled end 41 may additionally have a cross-shaped portion forming a T for aiding in the application of torque to the transverse rod 32.

Figure 7:
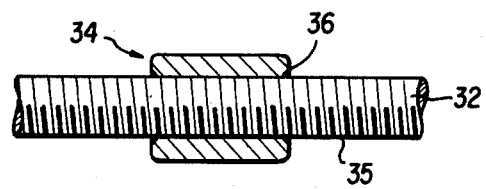
FIG. 7 is a partial cross-sectional view taken along lines 7—7 of FIG. 5 showing the thread engagement between the transverse rod and the transverse hook.

Referring to the sectional view of FIG. 7, it is readily apparent that the transverse rod 32 is threaded and threadably engages transverse hook 34. The general purpose of the transverse hook 34 is to engage and contact the Harrington distraction rod 5 illustrated in FIGS. 1 and 3. The internally machined threads 36 of the transverse hook 34 engage the transverse rod 32 so that rotation of the rod 32 moves the transverse hook 34 toward the basket hook 31 until the transverse hook 34 engages the Harrington distraction rod 5. Locking nut 33 similarly engages threaded transverse rod 32 so that when the final position of the transverse hook 34 is reached, the locking nut 33 may be rotated into locking contact with the transverse hook 34.

Figure 8:
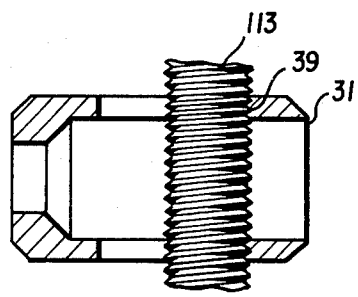
FIG. 8 is a partial cross section view of the basket hook engaging a Harrington compression rod.

One critical feature of the invention is the thread engagers 39 which form a part of the basket hook 31. Generally, the radius of curvature of the engaging portion 39a is equal to or greater than the radius of curvature of the cross section of the transverse rod 32. In addition, the engaging portion 39a is provided with thread engagers 39 and the threads of the Harrington compression rod 113. The exploded view illustrated in FIG. 8 clearly points out the engagement between the thread engagers 39 and the threads of the Harrington compression rod 113. This engagement is considered significant in that it prevents the basket hook 31 from sliding along the compression rod 11, a significant improvement over the prior art devices. It is understood that engaging means other than thread engagers 39 on the hook which correspond to a threaded rod could be used. Any convenient engaging means could be utilized on the engaging portion of the hook to cooperatively mate with a corresponding engaging means on the rod to thereby prevent movement of the basket hook 31 along the rod 113.

The method of employing the transverse tensioning apparatus of the invention is as follows. A Harrington distraction rod 5 is placed on the concave side of the spine and a Harrington compression rod 113 is placed on the convex side of the spine. Using a bone clamp or a similar instrument, the distraction rod and the compression rod are pulled toward each other achieving and maintaining the desired amount of transverse traction. The basket hook 31 is positioned on the compression rod 113 and the transverse hook 34 is advanced to its position tight against the distraction rod 5 by rotation of the knurled end 41 of the transverse rod 32. Conveniently, this rotation can be effected by movement between the thumb and index finger. The bone clamp is then released, leaving the transverse traction apparatus in place to maintain the correction and position desired between the Harrington compression and distraction rods. The locking nut 33 on the transverse rod 32 is then tightened down snugly against the transverse hook 34, securing its location. The excess threaded rod beyond the locking nut 33 is cut off and discarded. It is contemplated that more than one transverse traction apparatus may be used in the form of "rungs on a ladder" to join the Harrington distraction and compression rods down the spine, greatly increasing the rigidity of the spinal fixation. In addition, the use of a plurality of transverse traction devices adds to the correction already obtained with the distraction and compression rods by retaining the rods in parallel condition.

As is apparent by a close comparison between the invention and the prior art device as particularly disclosed in French Pat. No. 2,244,446, there are significant advantages to the invention. First of all, it is clear that the invention is essentially self contained. By turning the knurled end 41 of the transverse threaded rod 32, the transverse hook 34 is moved toward the basket hook 31. This avoids the need for several additional instruments, small set screws, etc. Of course, the swivel means 41 connecting the transverse rod 32 and the basket hook 31 forms the basis of allowing the transverse rod 32 to be rotated.

Second of all, the transverse hook 34 is threaded to engage the transverse threaded rod 32 which allows it to advance as the threaded rod is turned. This avoids the need to use set screws to jam the threads of the rod in order to positively secure the transverse hook 34 to the transverse threaded rod 32.

Third of all, the basket hook includes thread engagers at its hook portion so as to lock positively onto the threaded Harrington compression rod 113 which has been placed on the convex side of the scoliotic curvature of the spinal column. This prevents the hook from slipping down the compression rod, as is possible with the prior art devices.

Various changes may be made in the details of the invention, as disclosed, without sacrificing the advantages thereof or departing from the scope of the appended claims. For example, it is understood that the transverse tensioning device may be used to form a tensioning interconnection between any appropriate vertically positioned spinal rods, and not just the Harrington compression and distraction rods. Furthermore, although the present has been disclosed and discussed with particular regard to its exceptional advantages in terms of transverse traction devices for the correction of scoliotic curvature of the spinal column, it may be understood that each aspect of the invention may be employed in several surgical applications wherein engagement between rods is required. For example, it is contemplated that the transverse hook 34 may similarly be provided with thread engagers 39 to hold its position on the Harrington distraction rod, if the distraction rod is threaded. In addition, it is contemplated that a separate locking nut may be located on the transverse rod 32 between the transverse hook 34 and the basket hook 31 to further lock in position the transverse hook 34 and/or to further hold the position of the basket hook 31.

What is claimed is:

1. In an apparatus for the correction of scoliotic curvature of the spinal column, including a first vertically positioned spinal rod for engaging a concave side of the spinal column, a second vertically positioned spinal rod for engaging a convex side of the spinal column, and a tensioning means for engaging the first spinal rod and the second spinal rod, said tensioning means comprising:
   (a) a transverse threaded rod having first and second ends;
   (b) a basket hook;
   (c) a swivel means interconnecting the first end of the transverse rod and the basket hook, said swivel means allowing rotation of the transverse threaded rod about its longitudinal axis within the basket hook, said swivel means including a knob portion integrally connected to the first end of the transverse rod, said knob including a tapered portion, tapering outward from the transverse rod, and said basket hook including a seat of complementary shape to the knob for engaging the knob and easily allowing rotation of the knob within the seat; and
   (d) a hook means threadably engaging the transverse threaded rod between the first and second ends thereof whereby the basket hook engages one of the spinal rods and the hook means engages the other spinal rod and rotation of the transverse threaded rod about its longitudinal axis causes the first end of the transverse threaded rod to swivel within the basket hook and further causes the hook means to move along the transverse threaded rod due to the threading engagement between the hook means and the transverse threaded rod, thereby forming a tensioned interconnection between the first spinal rod and the second spinal rod.

2. The tensioning means of claim 1 wherein the second end of the transverse threaded rod has a knurled surface whereby the knurled surface may be grasped between an index finger and thumb and rotated.

3. The tensioning means of claims 1 or 2 wherein said basket hook has an engaging means on an internal surface thereof for engaging one of the spinal rods, and wherein said spinal rod includes a corresponding engaging means for cooperatively mating with the engaging means on the basket hook, thereby preventing movement of the basket hook along said spinal rod.

4. The tensioning means of claim 3 wherein said engaging means on the internal surface of the basket hook and said corresponding engaging means on said spinal rod are cooperatively mating thread engagers.

5. The tensioning means of claim 1 further including a locking means threadably engaging the transverse threaded rod between the first and second ends thereof whereby the locking means abuts the hook means to selectively hold the hook means in a desired position along the threaded rod.

6. In an apparatus for the correction of scoliotic curvature of the spinal column, including a first vertically positioned spinal rod engaging a concave side of the spinal column, a second vertically positioned spinal rod engaging the convex side of the spinal column, and a tensioning means for engaging the first spinal rod and the second spinal rod, said tensioning means including a transverse threaded rod having first and second hooks for engaging the spinal rods and for forming a tensioned interconnection between the spinal rods, the improvement comprising an engaging means on an interior surface of said first hook and a corresponding engaging means on the external surface of one of the spinal rods for cooperatively mating with the engaging means of the basket hook , thereby preventing relative movement between the first hook and the spinal rod which is engaged by the first hook.

7. In an apparatus for the correction of scoliotic curvature of the spinal column, including a first vertically positioned spinal rod for engaging a concave side of the spinal column, a second vertically positioned spinal rod for engaging a convex side of the spinal column, and a tensioning means for engaging the first spinal rod and the second spinal rod, said tensioning means comprising:
   (a) a transverse threaded rod having first and second ends;
   (b) a basket hook;
   (c) a swivel means interconnecting the first end of the transverse threaded rod and the basket hook, said swivel means allowing rotation of the transverse threaded rod about its longitudinal axis within the basket hook;
   (d) a hook means threadably engaging the transverse threaded rod between the first and second ends thereof whereby the basket hook engages one of the spinal rods and the hook means engages the other spinal rod and rotation of the transverse threaded rod about its longitudinal axis causes the first end of the transverse threaded rod to swivel within the basket hook and further causes the hook means to move along the transverse threaded rod due to the threading engagement between the hook means and the transverse threaded rod, thereby forming a tensioned interconnection between the first spinal rod and the second spinal rod; and (e) an engaging means on an internal surface of said basket hook for engaging one of the spinal rods, and wherein said spinal rod includes a corresponding engaging means for cooperatively mating with the engaging means on the basket hook, thereby preventing movement of the basket hook along said spinal rod.

8. The tensioning means of claim 7 wherein the second end of the transverse threaded rod has a knurled surface whereby the knurled surface may be grasped between an index finger and thumb and rotated.

9. The tensioning means of claim 7 wherein said engaging means on the internal surface of the basket hook and said corresponding engaging means on said spinal rod are cooperatively mating thread engagers.

10. The tensioning means of claim 7 further including a locking means threadeably engaging the threaded rod between the first and second ends thereof whereby the locking means abuts the hook means to selectively hold the hook means in a desired position along the threaded rod.

11. In an apparatus for the correction of scoliotic curvature of the spinal column, including a first vertically positioned spinal rod for engaging a concave side of the spinal column, a second vertically positioned spinal rod for engaging a convex side of the spinal column, and a tensioning means for engaging the first spinal rod and the second spinal rod, said tensioning means comprising:

(a) a transverse threaded rod having the first and second ends;

(b) a basket hook;

(c) a swivel means interconnecting the first end of the transverse threaded rod and the basket hook, said swivel means allowing rotation of the transverse threaded rod about its longitudinal axis within the basket hook; and (d) a hook means threadably engaging the transverse threaded rod between the first and second ends thereof whereby the basket hook engages one of the spinal rods and the hook means engages the other spinal rod and rotation of the transverse threaded rod about its longitudinal axis causes the first end of the transverse threaded rod to swivel within the basket hook and further causes the hook means to move along the transverse threaded rod due to the threading engagement between the hook means and the transverse threaded rod, thereby forming a tensioned interconnection between the first spinal rod and the second spinal rod and wherein said second end of the transverse threaded rod has a knurled surface whereby the knurled surface may be grasped between an index finger and thumb and rotated.

* * * * *